(12) United States Patent
Harrison (10) Patent No.: US 9,222,904 B2
(45) Date of Patent: Dec. 29, 2015

(54) METHOD AND APPARATUS FOR DETECTING TRACK FAILURE (71) Applicant: Harold Harrison, Friday Harbor, WA (US)

(72) Inventor: Harold Harrison, Friday Harbor, WA (US)

(*) Notice: Subject to any disclaimer, the term of this patent is extended or adjusted under 35 U.S.C. 154(b) by 67 days.

(21) Appl. No.: 13/966,219

(22) Filed: Aug. 13, 2013

(65) Prior Publication Data

US 2014/0044146 A1 Feb. 13, 2014

Related U.S. Application Data

(60) Provisional application No. 61/682,660, filed on Aug. 13, 2012.

(51) Int. Cl.
*G01L 5/00* (2006.01)
*G01N 25/72* (2006.01)
*G01M 5/00* (2006.01)
*B61L 23/04* (2006.01)

(52) U.S. Cl.
CPC ............. *G01N 25/72* (2013.01); *B61L 23/044* (2013.01); *B61L 23/047* (2013.01); *G01M 5/0025* (2013.01); *G01M 5/0041* (2013.01)

(58) Field of Classification Search
CPC .................. G01M 5/0025; G01N 2291/2623; B61L 23/042; G01K 13/00
USPC ................................ 73/760, 766, 862.01, 769
See application file for complete search history.

(56) References Cited

U.S. PATENT DOCUMENTS

| 5,161,891 | A | * | 11/1992 | Austill | 374/141 |
| 5,386,727 | A | * | 2/1995 | Searle | 73/602 |
| 7,502,670 | B2 | | 3/2009 | Harrison | |
| 7,869,909 | B2 | | 1/2011 | Harrison | |
| 8,155,809 | B1 | * | 4/2012 | Bilodeau et al. | 701/19 |
| 2007/0120665 | A1 | * | 5/2007 | Martin et al. | 340/545.1 |

* cited by examiner

*Primary Examiner* — Max Noori
(74) *Attorney, Agent, or Firm* — Eric G. Halsne

(57) ABSTRACT

A railroad track monitoring system is described which detects changes in rail track geometry that could lead to derailments, The changes in geometry are detected via analysis of temperature and stress parameters that are collected at one or more sensors installed on the track. Methods are described which provide faster detection and reduced false alerts, thereby saving time and expense to the railroad system.

17 Claims, 8 Drawing Sheets

METHOD AND APPARATUS FOR DETECTING TRACK FAILURE

BACKGROUND OF THE INVENTION

Monitoring railroad track safety and performance by sensing the Rail Neutral Temperature (RNT) or Stress Free Temperature (SFT) is known in the art. U.S. Pat. No. 7,502,670 entitled "System and Method for Determining Rail Safety Limits, for example, discusses methods of monitoring the RNT at a single point over a long period of time to determine changes in track geometry and strength. U.S. Pat. No. 7,502,670 and the related U.S. Pat. No. 7,869,909 are incorporated by reference.

Figure 1:
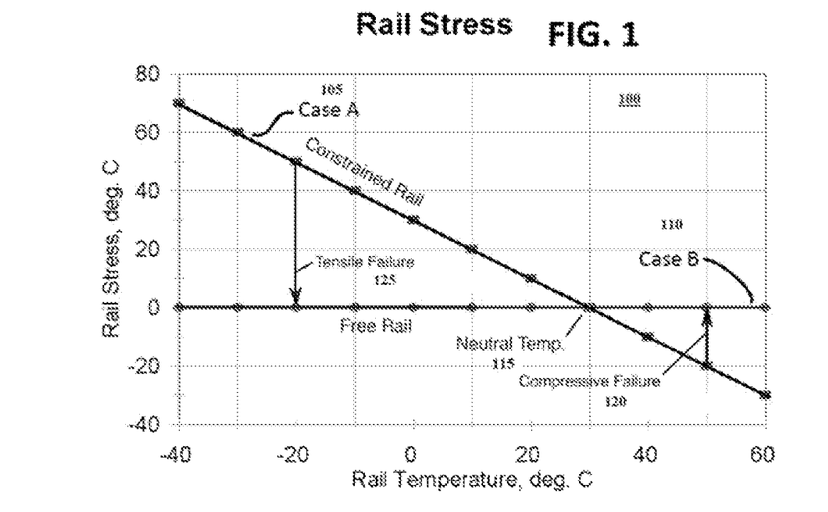
FIG. 1 illustrates a typical variation in stress of a rail portion with temperature, both in a constrained and free state.

FIG. 1 illustrates the concept of RNT and SFT over a range of temperatures, along the x axis, and mechanical stress, along the y axis, in graph 100. In this description, both rail stress and temperature are dimensioned in degrees Celsius. The RNT 115 is defined as the rail temperature at which the rail experiences zero stress. Rail temperatures above the RNT tend to create compression in a constrained rail. Rail temperatures below the RNT tend to create tension in a constrained rail.

Railroad rail incurs tensile and compressive stresses as it heats and cools under ambient temperature conditions. The rail typically behaves in a range between two limiting cases when installed in track. Limiting Case A 105 is the fully constrained case wherein all thermal energy absorbed or dissipated by the rail produces stresses proportional to temperature. On the ordinate, the units of stress are expressed in temperature degrees, which provides a −1 slope in the fully constrained case.

Limiting Case B 110 describes a rail that is completely free to expand/contract with temperature changes. Case B 110 is not normally observed in functional track except for very limited circumstances near bolted rail joints and/or special slip joints. In practice, Case A 105 most closely approximates the observed case with some small differences due to less than perfect constraints in the track structure. Each point on the two curves is determined from a point pair of stress and temperature.

Rail failure due to tensile longitudinal rail loads or track panel buckling due to compressive longitudinal rail loads have a common characteristic, i.e. with a greater magnitude of the stress and forces comes a higher the probability of a track failure. In either tension or compression, the probability is approximately linear. The probability of failure is also relatively low when below the design limits of the track. However, when the loads are some significant percentage of the design limits, then flaws in the rail, excessive impacts by rolling stock, or less than intended support conditions in the crossties/ballast may produce an unexpected failure.

Whether above or below design limits, a common circumstance occurs in every case where there is a failure. Mechanical energy is released from the rail system, causing the calculated RNT to collapse towards the stress free state. For failures in tension, e.g. rail breaks, as exemplified by arrow 125, tensile stresses are removed. For failures in compression, e.g. buckling failures as exemplified by arrow 120, compressive stresses are removed.

Figure 2:
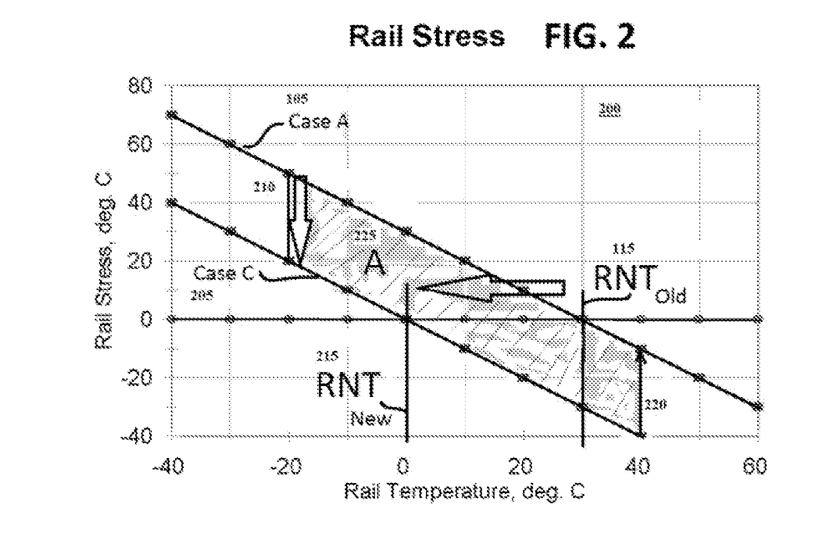
FIG. 2 illustrates possible changes in the stress-temperature curve in a rail portion caused by faults or elastic motion in the rail portion.
Figure 3:
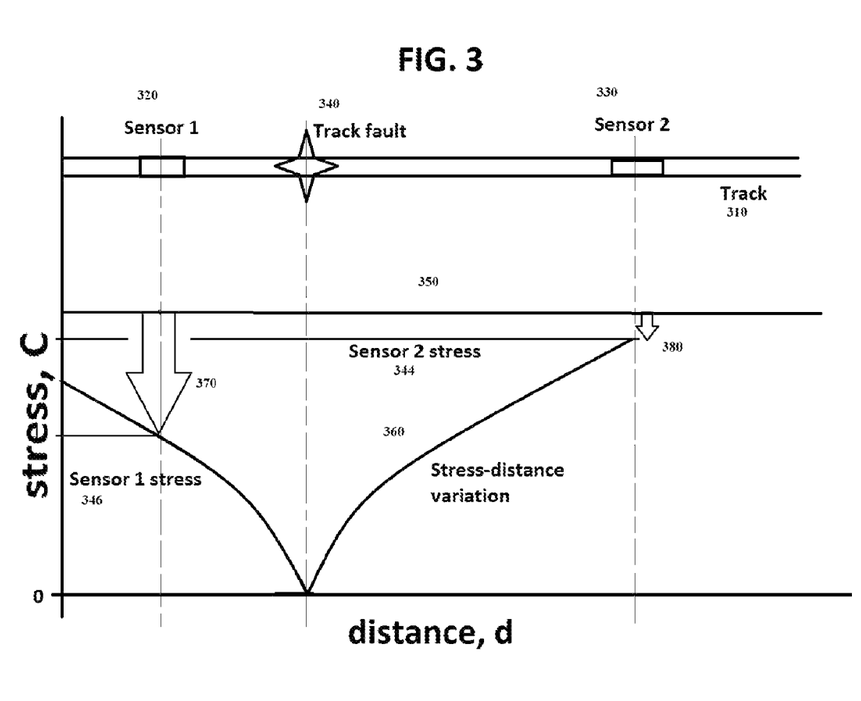
FIG. 3 illustrates the sensed response in a system for identifying railroad track faults comprising two or more rail mounted sensors.

In addition, referring briefly to FIG. 3, the closer the point of measurement is to the point of failure, the closer the post failure state will be the true (new) RNT. The FIG. 2 graph 200 illustrates the situation where a tensile rail stress failure is measured at a distance from the break location. Case C 205 illustrates a typical observed RNT curve in which a release of stress due to a track failure essentially shifts the Case A 105 down by the amount of stress release at 210, and where the new RNT 215 is lower than the pre-failed RNT 115. It can easily be observed in FIG. 2 that the opposite case can be true: If Case C 205 results in a compressive failure, energy is released by buckling and a reduction in compressive stresses occurs at 220. The RNT 215 in this case would increase to RNT 115.

In the case of a tensile failure of the track very near the point of measurement, the vertical drop is to the zero stress Case B curve. In the case of a complete buckling failure, the 'jump' up to the zero stress state to the Case B curve occurs.

In either of the failure cases, the data point pairs will be clearly different than any prior history that may have been collected. Therefore such a failure can only be predicted by monitoring both of temperatures and stresses.

Both of the above-described patents utilize the above-described concepts in a system and method that issues an alert if a long-term change in RNT is of sufficient magnitude. The prior art system and method is forced to rely on long-term changes in RNT because the system is susceptible to noise and elastic rail behavior, e.g. periodic geometric cycling of the rail due to temperature and elastic movement on the rail bed. These factors prevent the prior art systems and methods from identifying rail track faults in real time, e.g. shortly after a rail failure has occurred. Such a system is needed in order to improve rail safety, reduce the costs of maintenance, and to reduce failure-related downtime.

SUMMARY OF THE INVENTION

The present invention is a system and method for quickly identifying faults induced in railroad track sections caused by temperature changes or mechanical failures. The methods described herein enable reliable alarming in real time by detecting a sudden change in RNT. In the context of the invention, the time frame for detecting a change in RNT is approximately ten minutes or less, whereas the prior art systems commonly required hours or even days of collecting data to reliably detect failures.

According to one embodiment of the invention, a system for detecting a rail breakage in a track portion of a railroad comprises first and second sensors at first and second locations respectively, each operable to obtain the longitudinal stress data and the temperature data at that location. Computer memory in communication with the sensors stores the data. A rail processor in communication with the computer memory is operable to detect a rail fault in essentially real time, i.e. 10 minutes or less, based upon the stress and temperature data from both sensors.

According to another embodiment of the invention, a method is described for detecting a fault in a track panel which includes a rail portion of a railroad. The method comprises the steps of obtaining longitudinal stress data and temperature data at two separate locations on a rail portion, determining the RNT along the rail portion, and detecting a change in RNT at both of the locations. A simultaneous change at both locations indicates a rail fault, so the method includes the step of issuing an alert based on the detecting step.

According to another embodiment of the invention, a system for detecting a rail breakage in a track portion of a railroad comprises at least one sensor disposed at a rail location, operable to obtain the longitudinal stress data and the temperature data at that location. The system time-averages a plurality of measured RNT values and compares the average to an initial RNT. If the difference exceeds a threshold, the system issues a rail failure alert. If the threshold is not exceeded, the initial RNT value may be adjusted based on a function of the measured average. The system thereby reduces error caused by signal noise in the sensor data, such as rapid temperature changes induced by rain on the rails. Also described is a related method for detecting a fault in a track panel which includes a rail portion of a railroad. The method comprises the steps of determining a target rail neutral temperature (RNT) for the rail portion, collecting longitudinal stress data and temperature data of the rail portion over a predetermined period of time, determining a set of RNT values based upon the collecting step, time averaging the determined set of RNT values over the predetermined period of time to obtain an average RNT, comparing the average RNT to a predetermined threshold, and issuing a rail failure alert step based on the comparing averaging step.

According to yet another embodiment of the invention, a method is described for determining the stability of a rail portion of a railroad, comprising the steps of monitoring rail stress and temperature over one or more temperature cycles, calculating a hysteresis curve of stress and temperature, determining a rail stability factor based upon the hysteresis curve, and outputting the stability factor for use in rail maintenance planning The hysteresis curve can comprise a portion of the stress temperature cycle or a complete hysteresis loop.

According to yet another embodiment of the invention, a method is described for adjusting a failure prediction model for a rail portion, comprising the steps of detecting a sudden change in RNT, calculating new failure stress and temperatures based upon the new RNT, and adjusting the failure prediction model using the new failure stress and temperature thresholds.

DETAILED DESCRIPTION OF THE EMBODIMENTS

Now with reference to the FIGUREs, if an array of data sensors is distributed along the rail track, the inventors have observed that any two adjacent sensors will detect a failure condition in the vicinity of the sensors. In prior systems, a single point failure of any one sensor may induce a jump of signal away from the RNT condition, which is counter to expectations. If the jump emulates the track failure, a false alarm might result. But if two sensors see the same jump condition at the same time, then there is a high probability that the jumps are valid alarms, even if the jumps are not of the same magnitude.

FIG. 3 illustrates the detection by two sensors 320, 330 of the same track fault 340, which is a rail break fault in this example. Prior to the fault, each of sensor 1 320 and sensor 2 330 are installed on track portion 310. Just prior to the fault, each of the sensors 320, 330 sense a similar stress in the rail at the then-existing track temperature. When the track fault occurs, the RNT at the fault location falls towards the zero longitudinal stress value" or "zero stress value. However, because of intervening constraining devices such as cross-ties and ballast, some longitudinal stress may remain in the rail at the sensor 1 and sensor 2 locations, as defined by stress-distance variation curve 360. Depending on the distance from the fault and the conditions in-between, sensor 1 stress 346 and sensor 2 stress 380 may differ substantially in magnitude. But they will change in the same direction 370, 380 and at the same time.

Figure 6:
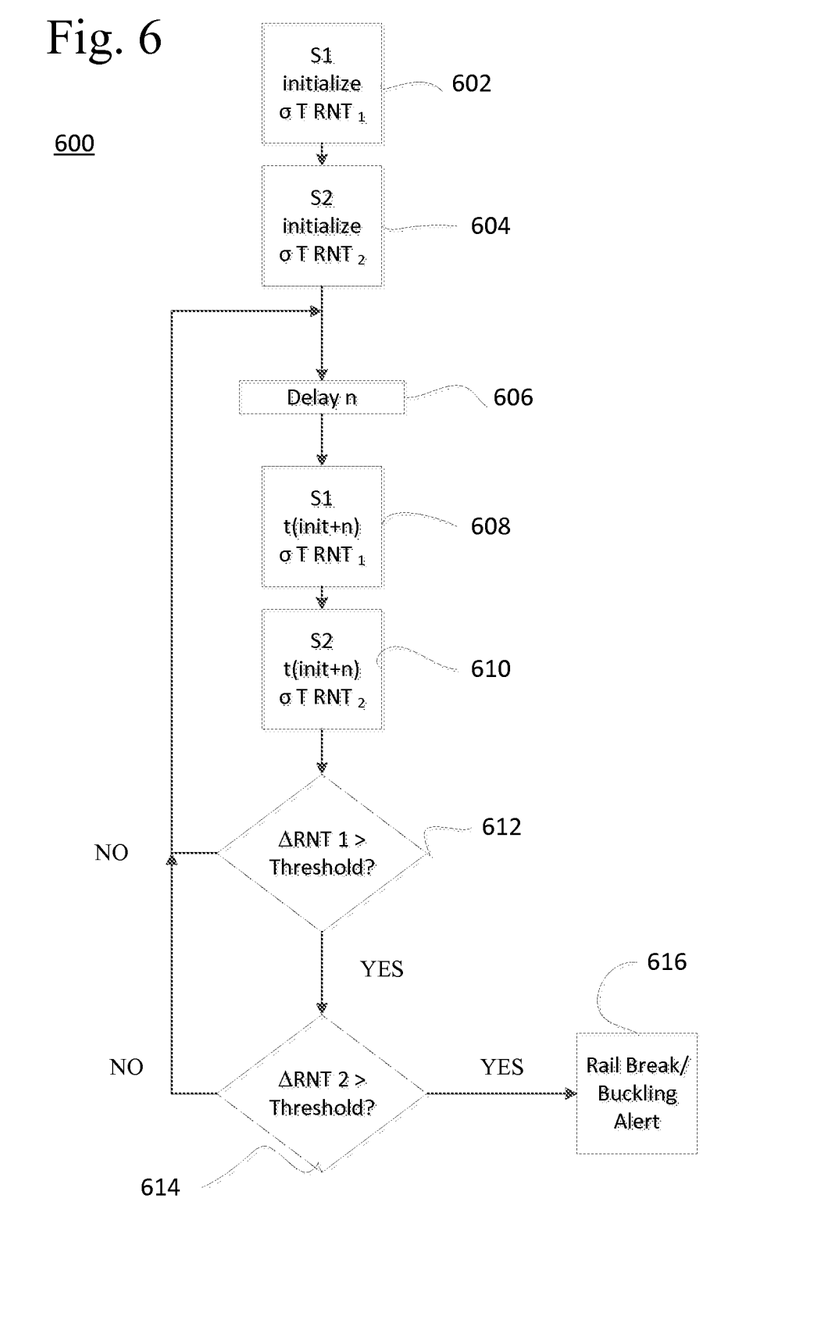
FIG. 6 illustrates a flow diagram of a method for detecting a rail break in a railroad track portion, using two or more sensors located at different locations.

The FIG. 6 flowchart illustrates a method that adopts the concepts described in FIG. 3 for detecting a rail failure in real time and with increased accuracy. Sensors S1 and S2 are arranged at different locations on a rail portion, and are disposed to sense longitudinal stress $\sigma$ and rail temperature T, which thereby determine the RNT at each location at steps 602 and 604. Each RNT 1 and RNT 2 is stored in memory for subsequent use. After predetermined delay period n at step 606, i.e. at time t(initial+n), longitudinal stress $\sigma$ and rail temperature T are again measured at S1 and S2, along with determinations of RNT, steps 608 and 610. The values are again stored in memory.

At step 612, the two RNTs from sensor S1 are compared. If the difference is within a predetermined threshold, no rail failure is indicated, and the process loops back to measure at the next time t(init+2n). However, if the difference exceeds a predetermined threshold, further analysis is needed to confirm a rail failure. At step 614, the two RNTs from sensor S2 are compared. If a rail failure has occurred, it would be expected that a change in RNT from S2 would exceed a threshold at the same time as S1. Therefore, if the RNT change in S2 also exceeds the threshold, rail failure is indicated at a high confidence. A rail break or buckling alert is then issued at step 616. If no/minimal RNT change in S2 occurs, then the anomaly in S1 may be due to a sensor failure, signal noise, or a transient condition at that location. In this case, the process loops back as before.

The predetermined threshold can be established easily by one of ordinary skill in the art, based upon a historical range of RNT variation at each location (in non-failure conditions), distance between sensors, historical experienced noise levels, typical weather conditions, rail portion construction methods and the like.

Figure 4:
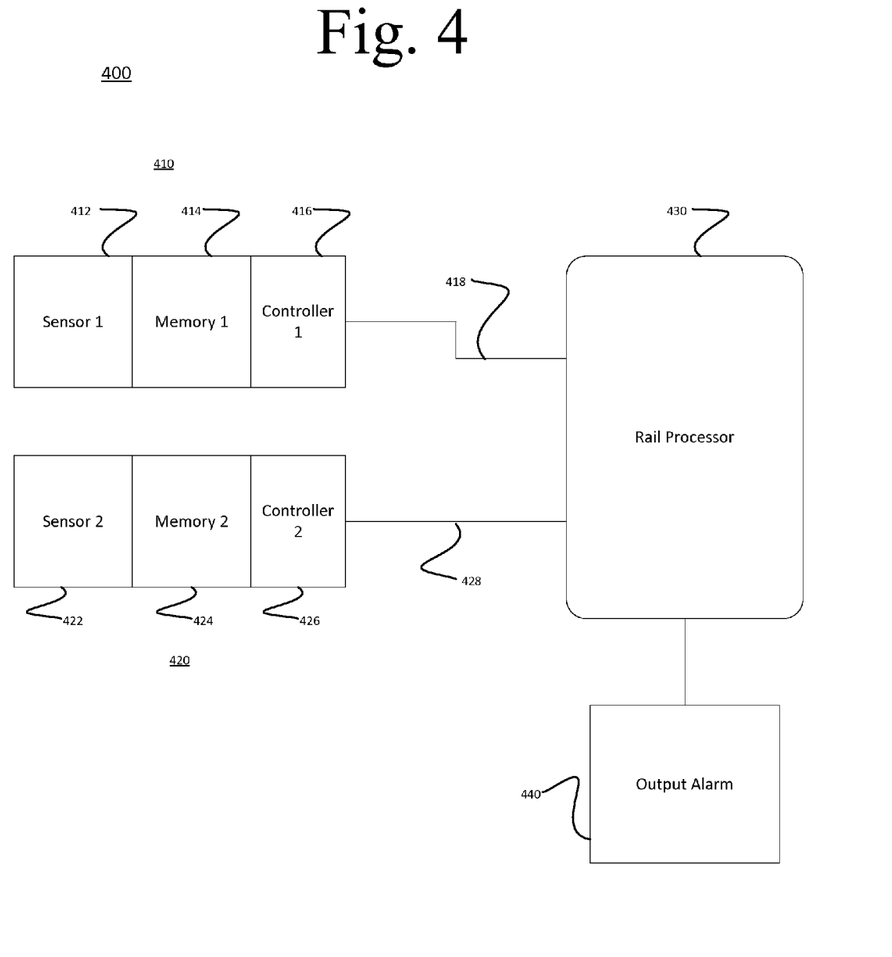
FIG. 4 is a function block diagram of a system for identifying railroad track faults.

FIG. 4 illustrates a monitoring system 400 for identifying railroad track faults within a track panel. The system includes two sensor modules 410, 420 disposed at two different locations along a rail portion of the track panel. Sensor module 410 includes a sensor 412 for measuring rail longitudinal stresses and rail temperature data. Each data point is stored in memory 414. Optional controller 416 may be operable to calculate intermediate figures such as RNT using the memory 414 data, and may also be operable to transmit the data to rail processor 430. Transmissions may be controlled on demand from processor 430, or may be transmitted automatically on a schedule by controller 416. A communication path 418 conveys the data between sensor 410 and processor 430. Preferably, path 418 is wireless.

Sensor module 420 is arranged similarly to module 410 but at a different location. Sensor 422, memory 424, controller 426 and communication path 428 similarly to those named in sensor module 410.

Rail processor 430 collects stress and temperature data, and optionally RNT data from each sensor module 410, 420 and employs the method described in the FIG. 6 flow chart to determine whether a rail failure has occurred. If a failure is determined, rail processor 430 issues an alert at output alarm 440. Output alarm 440 may comprise any of an annunciator, a visual message, a warning light. The warning may be variable to indicate the type, age and severity of the failure.

Figure 5:
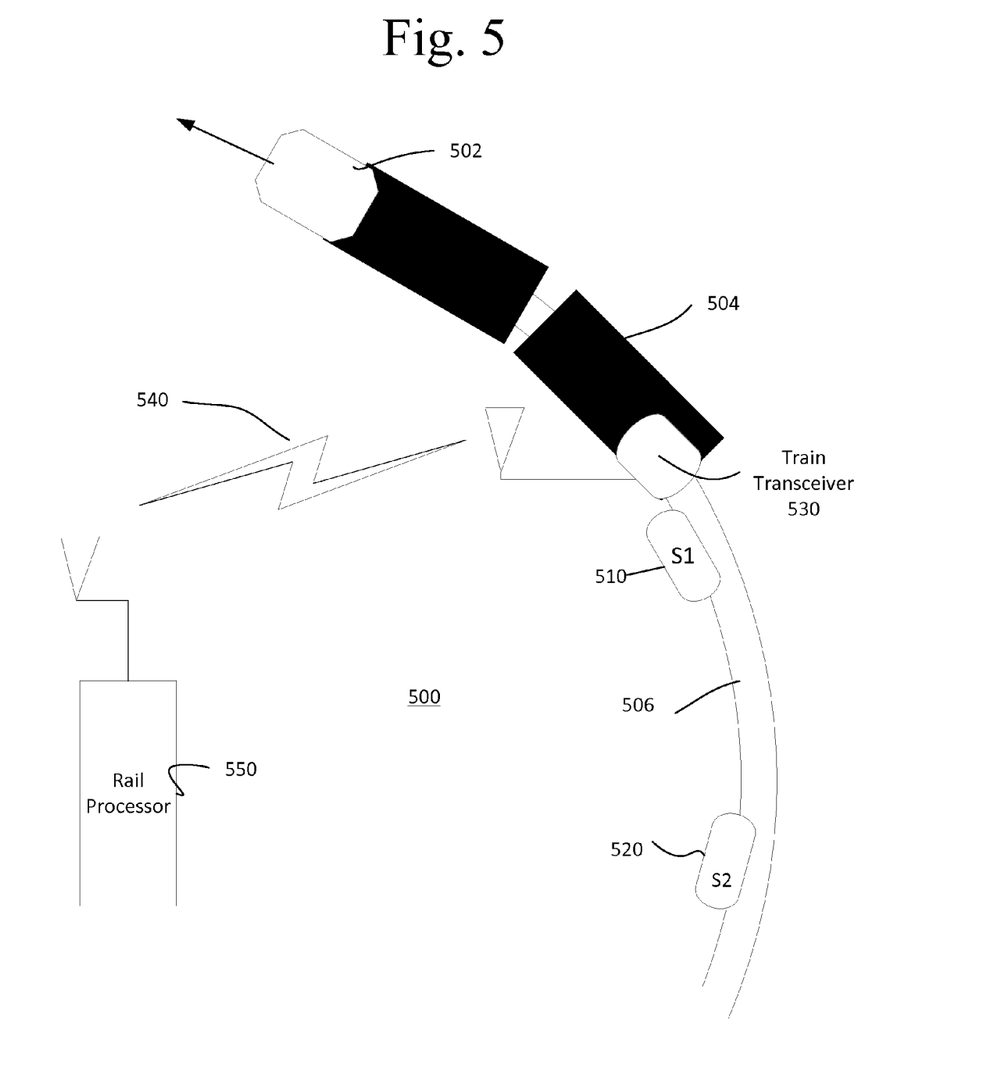
FIG. 5 illustrates another embodiment of the FIG. 4 system, wherein a communications path between the rail sensors and the processing system includes a train-mounted transceiver.

FIG. 5 illustrates another embodiment of the FIG. 4 system, except that a single communications path is employed between each sensor and the rail processor. In this embodiment, a transceiver 530 is disposed on a train 502, shown in FIG. 5 at the trailing end. However, transceiver 530 locations at other positions on the train may be even more advantageous in terms of personnel access, supply of power, and the like. Sensor modules 510, 520 are disposed similarly to those in FIG. 4, having memory 414, 424 and controllers 416, 426 respectively. Transceiver 530 queries each of sensor modules 510 and 520 via the rescpective controller 416, 426 as it passes by, which prompts the sensor modules 510, 520 to wirelessly transmit their time-stamped data to the transceiver 530. Transceiver 530 then transmits the sensor data to a remote centralized rail processor 550 via a wireless communications path 540.

The FIG. 5 embodiment 500 has several advantages over a static system. By bringing the transceiver to the sensors, less battery power for data transmission is required in each sensor. The single transceiver which can query a large number of sensor modules installed along the track is cost-effective. In addition, by gathering data from each sensor during the train's passing, faults that may have been induced by the train itself can be sensed.

Figure 7:
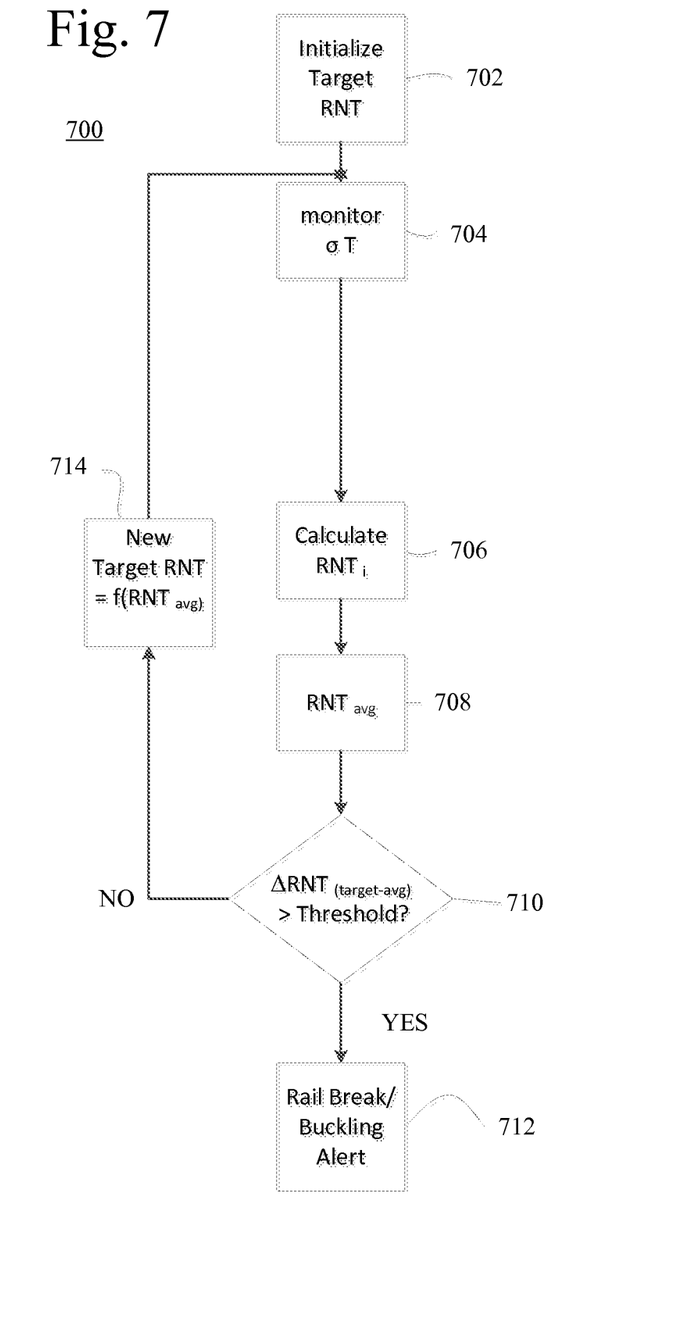
FIG. 7 illustrates a flow diagram of a method for detecting a rail break in a railroad track portion using one or more sensors, using a time-averaged monitored RNT value.

Now referring to the flowchart of FIG. 7, another embodiment of an improved method for detecting a rail break or compressive buckling is described. In some track conditions, particularly if bolted joints or other anomalous non-continuous conditions are affecting locally-normal stress-temperature curves (between Case A 105 and Case B 110 limits in FIG. 1), a noisy data space will be produced that can still be reliably alarmed on. It can be shown that by filtering the immediate trend by averaging two or more RNT values computed from immediately previous readings, allowing for a smaller delta stress reading being reliable. (These readings are typically on the order of ten minutes apart, or less, if real-time train safety is a factor.) Deeper averages performed within the module may also characterize the track performance without infringing on the external trending claimed in the base patent. Internally stored daily cycles can be trended to note typical nominal and min/max limits to RNT variation throughout each day. Again this can reduce the likelihood of false alarming, which allows for detecting smaller drops in stress and/or greater distances between sensors.

One or more sensors are employed by the method 700 shown in FIG. 7. The method is initialized at step 702 with a predetermined target RNT. Monitoring of temperature T and longitudinal stress σ begins at intervals i at step 704. An RNT at each interval i is then calculated and stored in memory at step 706. A predetermined number of the interval RNTs are averaged at step 708 and the average is compared against the target RNT. If the difference exceeds a predetermined threshold at decision step 710, then a rail failure is indicated. If not, a new target RNT may be generated at step 714 as a function of the average RNT, and the process repeats.

The averaging of RNTs prior to comparing to a target RNT enables the reduction of signal noise from transient conditions in the rail system. Adjusting the target RNT at step 714 accounts for long-term drift in the system, while retaining the ability to capture sudden reductions in RNT. Thus, the FIG. 7 method provides an more accurate measurement of the trends in RNT.

Figure 8:
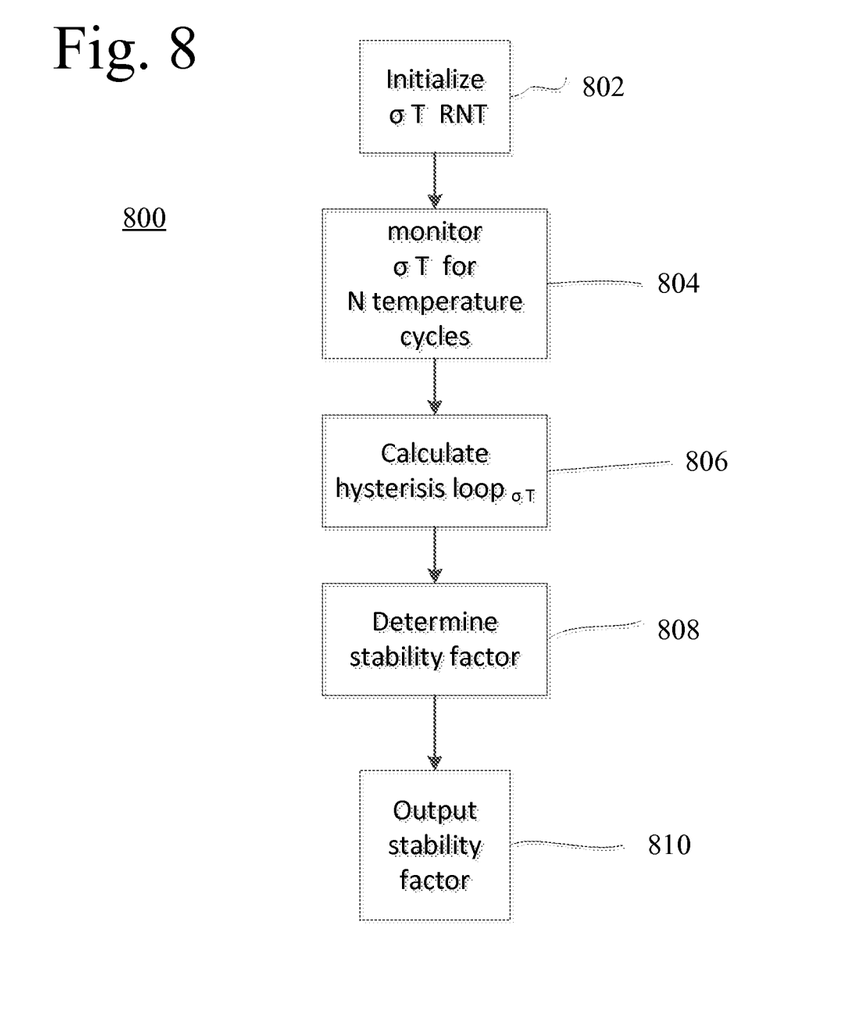
FIG. 8 illustrates a flow diagram of a method for determining the stability of a railroad track portion, using a detected hysteresis curve of stress and temperature over at least one temperature cycle.

FIG. 8 illustrates a method for determining a geometric stability factor for a rail portion of a railroad. Instability commonly arises, for example, in the curved sections of a rail portion. In cold weather that induces tensile stress in the rail, the induced stress tends to pull the curved sections in, i.e. to shorten the path around the curve. Following warm weather tends the opposite: to push the curved sections out, i.e. to lengthen the path around the curve. If the track is not entirely constrained, the stress-temperature curve over daily cycles of warm and cold weather appear as a hysteresis loop. Area A 225 of FIG. 2 illustrates such a hysteresis loop. The area formed by the hysteresis loop indicates the level of track stability at that rail section, which may appear to shift elastically during a daily temperature cycle, and returns to the initial geometry each day. But if unstable enough, the rail section may break from tensile stress exceeding a limit in cold weather, or may sun-kink in warm weather. Either situation can lead to a derailment.

A similar measure of stability is some portion of the lower bound of the daily hysteresis curve measured against the purely constrained −1 slope curve. The second curve can be described as a percent of maximum slope measure.

The FIG. 8 method 800 proceeds by initializing the system at step 802 and then monitoring temperature T and longitudinal stress σ over one or more temperature cycles at step 804. Typical temperature cycles are daily, but others may be used. A hysteresis loop is calculated at step 806, using the cycle data of stress and temperature. At step 808 a stability factor is calculated as a function of the area within the hysteresis loop, or as a function of a maximum slope measure. The calculated stability factor is output to the user at step 810, and may be used to ascertain whether a particular rail portion requires stabilization work or not.

Figure 9:
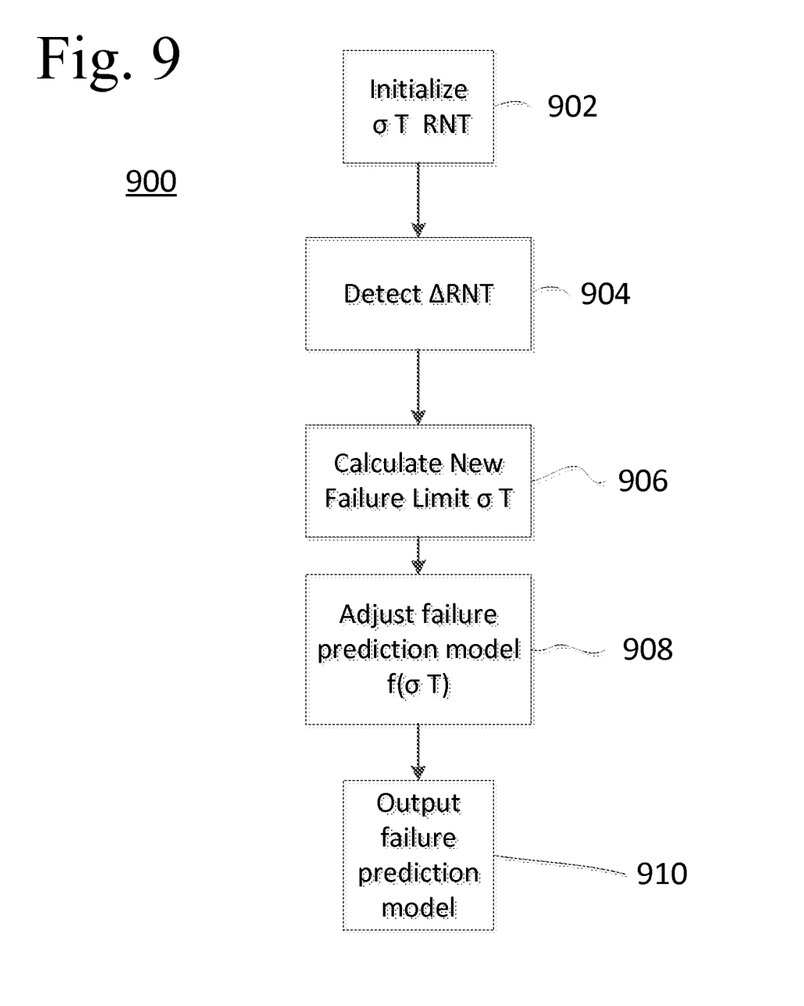
FIG. 9 illustrates a flow diagram of a method for improving a failure prediction model for a railroad track portion, incorporating data obtained subsequent to a detected change in the RNT.

FIG. 9 illustrates yet another useful embodiment of a method for improving the accuracy of a rail track failure predication model, especially after a sudden change in RNT is detected. A basic 'fall to zero' stress concept is employed by this method. With a simple 24 hour summary of the RNT as a baseline and a partial 'fall to zero' drop in stress at a particular temperature, a unique 'soft fail' condition can be quantified. In particular, if a sensor is in a curve and the temperatures are very low such that the track panel will tend to shift towards the center of the curve, that reduction in RNT, similar to Case C 205 in FIG. 2, will indicate that the track panel has shifted inward and the stress at which it occurred establishes the failure limit of the tie/ballast infrastructure. So both the panel shift and the threshold strength of the local infrastructure can be identified. The latter datum is important because track modeling used in the prior art database uses generic parameters of track component properties to compute a probable strength limit. This relies on many uncertainties leading to a wider margin of error in predicting future track behavior. Detecting and recording a partial 'failure' in track (primarily tie/ballast interaction) allows the fault detection system to develop a closed system calibration that substantially increases the accuracy of future safety limit predictions.

The FIG. 9 method 900 begins at initialization step 902, and thereafter temperature T and longitudinal stress σ are monitored until the calculated RNT indicates a sudden change caused by a rail portion failure at step 904. In this case, the failure is indicated by a sudden change in RNT to a new value, such as that illustrated from Case A 105 to Case C 205 in FIG. 2. As can be seen in FIG. 2, the new curve associated with Case C 205 will have some temperature value which corresponds to the same rail stress failure value shown at the top of arrow 210. This new temperature value is easily calculated at step 906. Combined with the now-known failure stress level, the rail portion failure prediction model is adjusted at step 908 to reflect the new geometry of the rail portion. The adjusted mode is output at 910 for use in predicting when and where a particular rail system will fail in the future.

What is claimed is:

1. A system for monitoring a track panel which includes a rail portion on a railroad, comprising:
    a first sensor operable to obtain the longitudinal stress data and the temperature data of the rail portion at a first location at a time t;
    a second sensor operable to obtain the longitudinal stress data and the temperature data of the rail portion at a second location at the time t;
    one or more computer memories for storing the longitudinal stress data and temperature data obtained by the first and second sensors; and
    a rail processor in communicative connection with the computer memories, wherein the rail processor is operable to obtain the stress and temperature data obtained by both of the first and second sensors and to detect a rail fault in real time based on the stress and temperature data obtained by both of the first and second sensors,
wherein the rail processor is operable to determine the rail neutral temperature (RNT) corresponding to the longitudinal stress data and the temperature data at each of the first and second locations, and wherein the rail processor is further operable to detect a rail failure as a function of a simultaneous change in both of the first and second location RNTs.

2. The system of claim 1, wherein the communicative connection between the rail processor and the computer memories comprises a first wireless communications path that conveys the stress and temperature data from the first sensor to the rail processor and a second wireless communications path that conveys the stress and temperature data from the second sensor to the rail processor.

3. The system of claim 1, further comprising an output alarm operable to issue an alert based upon a detected rail fault.

4. The system of claim 1, wherein the communicative connection between the rail processor and the computer memories is a single communications path that comprises:
    a first and a second controller disposed in communication with the respective one or more computer memories, and operable to receive a data transmission query and further operable to wirelessly transmit the longitudinal stress data and the temperature data from the respective computer memory in response to a received query;
    a transceiver operable to sequentially query the first and second controllers when in proximity to the controllers, and further operable to wirelessly receive the transmitted longitudinal stress data and the temperature data, and further operable to wirelessly transmit the received longitudinal stress data and the temperature data to the rail processor.

5. The system of claim 4, wherein the transceiver is arranged to be mounted on a train that is movably positioned on the rail portion.

6. A method for detecting a fault in a track panel which includes a rail portion of a railroad, comprising the steps of:
    obtaining the longitudinal stress and the temperature of the rail at a first location at a time t;
    obtaining the longitudinal stress and the temperature of the rail at a second location at the time t;
    determining a rail neutral temperature (RNT) for the rail portion at both of the first and second locations based upon the respective obtaining steps;
    detecting a simultaneous change in RNT at both of the first and second locations; and
    issuing an alert of a rail fault based on the detecting step.

7. The method of claim 6, further comprising the step of comparing the detected change in RNT at both of the first and second locations to a predetermined threshold, wherein the issuing step is further based on the comparing step.

8. The method of claim 6, wherein the obtaining steps and the determining step are repeated after a predetermined delay period.

9. The method of claim 6, wherein the detecting step detects the change in RNT at both of the first and second locations in real time.

10. The method of claim 8, wherein the predetermined delay period is approximately ten minutes or less.

11. The method of claim 6, wherein the predetermined threshold is determined based upon one of a historical range of RNT variation, the distance between the first and second sensors, a historical noise level, an expected weather condition, and a rail portion characteristic.

12. A method for determining a geometric stability of a track panel which includes a rail portion of a railroad, comprising the steps of:
    obtaining longitudinal stress data and temperature data of the rail at a location on the rail portion;
    determining an initial rail neutral temperature (RNT) for the rail portion;
    collecting subsequent longitudinal stress data and temperature data for the rail portion over a predetermined period of time which includes at least one temperature cycle;
    calculating one of a hysteresis loop or a hysteresis curve based upon the collecting step; and
    determining a stability factor for the rail portion based on the determining, the collecting, and the calculating steps.

13. A method of claim 12, wherein the determining step is further based upon the calculated hysteresis loop.

14. The method of claim 13, wherein the calculating step further comprises calculating the area of the hysteresis loop, and further wherein the determining step is based upon the area of the hysteresis loop.

15. The method of claim 12, wherein the determining step is further based upon the calculated hysteresis curve.

16. The method of claim 12, further comprising a step of outputting the stability factor to a user.

17. The method of claim 12, wherein the predetermined period of time is one day.

* * * * *